United States Patent [19]

Feit et al.

[11] 3,989,745
[45] Nov. 2, 1976

[54] BENZOYL-BENZOIC ACID DERIVATIVES

[75] Inventors: Peter Werner Feit, Gentofte; Ole Bent Tvaermose Nielsen, Vanlose; Herta Bruun, Graested, all of Denmark

[73] Assignee: Lovens Kemiske Fabrik Produktionsaktieselskab, Ballerup, Denmark

[22] Filed: June 7, 1974

[21] Appl. No.: 477,180

[30] Foreign Application Priority Data
June 22, 1973  United Kingdom............... 29875/73

[52] U.S. Cl............................. 260/517; 260/294.8 G; 260/294.9; 260/295 AM; 260/332.2 A; 260/465 D; 260/470; 260/473 R; 260/476 R; 260/516; 260/518 R; 260/520 E; 424/263; 424/275; 424/324
[51] Int. Cl.².................................... C07C 65/20
[58] Field of Search................ 260/518 R, 520, 517

[56] References Cited
OTHER PUBLICATIONS
Noller, "Chemistry of Organic Compounds", 3rd ed. (1965), p. 259.

Primary Examiner—James O. Thomas, Jr.
Assistant Examiner—A. Siegel
Attorney, Agent, or Firm—Jackson, Jackson and Chovanes

[57] ABSTRACT

The present invention relates to a series of new compounds, their salts and esters and to methods for the preparation of the compounds having the general formula:

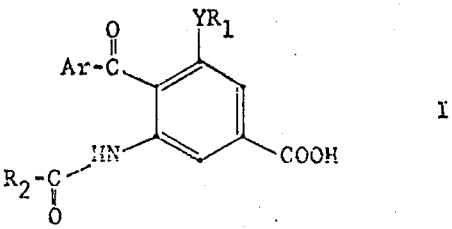

in which $R_1$ represents a straight or branched $C_1$–$C_6$ alkyl, alkenyl or alkynyl radical, or a $C_1$–$C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; $R_2$ stands for hydrogen or a straight or branched $C_1$–$C_6$ alkyl, alkenyl, alkynyl or alkoxy radical, optionally being substituted with halogen, a lower alkoxy or di-(lower alkyl) amino radical; Ar stands for a phenyl radical, optionally being substituted with halogen, lower alkyl, or lower alkoxy; Y stands for oxygen, sulphur or a methylene radical.

The compounds of the invention which are valuable in the human and veterinary practice, possess a pronounced diuretic and/or saluretic activity.

7 Claims, No Drawings

BENZOYL-BENZOIC ACID DERIVATIVES

This invention relates to a series of new compounds, their salts and esters and to methods for the preparation of the compounds which are valuable in the human and veterinary practice and have the general formula:

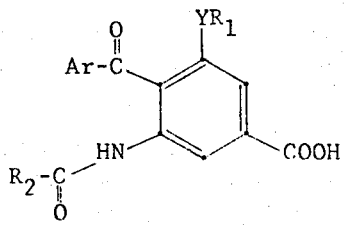

in which $R_1$ represents a straight or branched $C_1$–$C_6$ alkyl, alkenyl or alkynyl radical, or a $C_1$–$C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; $R_2$ stands for hydrogen or a straight or branched $C_1$–$C_6$ alkyl, alkenyl, alkynyl or alkoxy radical, optionally being substituted with halogen, a lower alkoxy or di-(lower alkyl) amino radical; Ar stands for a phenyl radical, optionally being substituted with halogen, lower alkyl, or lower alkoxy; Y stands for oxygen, sulphur or a methylene radical.

In particular, $R_1$ may represent e.g. a methyl, ethyl, propyl, isopropyl, butyl, isobutyl or tert-butyl radical, or one of the different isomeric pentyl, or hexyl radicals, an allyl, or propargyl radical, a benzyl, a phenethyl, a phenylpropyl, or 2-, 3-, or 4-trifluoromethylphenylmethyl radical, a 2-, 3-, or 4-methoxyphenylmethyl radical, a 2-, 3-, or 4-pyridylmethyl, 2- or 3-furylmethyl, 2- or 3-thienylmethyl, thiazolylmethyl, or imidazolylmethyl radical; or one of the corresponding ethyl radicals.

In particular, $R_2$ may represent hydrogen, or a methyl, ethyl, methoxy or ethoxy radical.

The substituents $R_1$, $R_2$ and Ar of formula I can be further substituted in different positions with different groups, such as one or more halogen atoms, e.g. chlorine or bromine atoms, lower alkyl, halo-lower alkyl, e.g. trifluoromethyl; amino groups, optionally being alkylated or acylated; hydroxy groups, which may be etherified, e.g. lower alkoxy, such as methoxy, ethoxy, n-propoxy, isopropoxy, n-butoxy or isobutoxy, or esterified with lower aliphatic carboxylic acids, such as lower alkanoic acids, e.g. acetic, propionic or pivalic acid, lower alkenoic acids, e.g. acrylic or methacrylic acid, or with lower aliphatic dicarboxylic acids, e.g. oxalic, malonic, succinic, glutaric, adipic, maleic or fumaric acid or their acid esters with lower alkanols, e.g. methanol or ethanol; or etherified mercapto groups such as methylthio, ethylthio, isopropylthio, butylthio or isobutylthio radicals.

Whenever the expression 37 lower" is used in the foregoing and in the following in connection with an organic radical it indicates a content of from 1 to 6 carbon atoms.

Of particular value are the compounds of the invention in which $R_1$ is selected from the group consisting of straight or branched $C_3$–5 alkyl radicals, and a methyl radical being substituted with phenyl, furyl, thienyl, and pyridyl, and the correspondingly substituted ethyl radicals.

The salts of the compounds of the invention are pharmaceutically acceptable salts, and include, for example, alkali metal salts, alkaline earth metal salts, the ammonium salt, or amine salts formed, for instance, from mono-, di- or trialkanolamines or cyclic amines. The esters of the compounds are preferably derived from lower aliphatic alcohols, cyanomethanol and benzyl alcohol.

It has been found that the compounds of the invention possess a pronounced diuretic and/or saluretic activity, which is surprising in view of the chemical structure and the replacement of a sulphamyl group with an amido function. The very low excretion of potassium ions and low toxicity also make the present compounds particularly valuable in human and/or veterinary practice.

Further the compounds of the invention are also extremely valuable in the treatment of patients suffering from hypersensitivity towards sulfanilamide diuretics and metanilamide diuretics because there exists no cross hypersensitivity between those compounds and the compounds of the invention.

The present compounds are effective after oral, enteral or parenteral administration, and are preferably prescribed in the form of tablets, pills, dragees, or capsules containing the free acid or salts thereof with atoxic bases, or the esters thereof, mixed with carriers and/or auxiliary agents.

Salts, which are soluble in water, may with advantage be administered by injection. The compounds of the invention are useful in the treatment of oedematous conditions, e.g. cardiac, hepatic, renal, lung, and brain oedema, or oedematous conditions during pregnancy, and of pathological conditions which produce an abnormal retension of the electrolytes of the body, and in the treatment of hypertension.

Another object of the invention resides in the selection of a dose of one of the compounds of the invention or their salts or esters which can be administered so that the desired activity is achieved without simultaneous secondary effects. In such a dosage unit the compounds are conveniently administered as a pharmaceutical preparation containing from 0.5 mg to 100 mg of the active compound. The compounds of formula I are preferably administered in amounts from 1 mg to 50 mg. By the term "dosage unit" is meant a unitary, i.e. a single dose capable of being administered to a patient, and which may be readily handled and packed, remaining as a physically stable unit dose, comprising either the active material as such or in a mixture of it with a pharmaceutical carrier and auxiliary agents.

In the form of a dosage unit the compounds may be administered one or more times a day at appropriate intervals. The daily dose usually amounts to from 2 to 50 mg always depending, however, on the condition of the patients and according to the prescription of the medical practitioner.

In pharmaceutical compositions containing the compounds of the invention, organic or inorganic, solid or liquid carriers suitable for oral, enteral, or parenteral administration can be used to make up the composition. Gelatin, lactose, starch, magnesium stearate, talc, vegetable and animal fats and oils, gum, polyalkylene glycol, or other known carriers for medicaments are all suitable as carriers.

In the pharmaceutical compositions, the proportion of therapeutically active material to carrier substances can vary between 0.5 per cent and 90 per cent.

The compositions may further contain other therapeutic compounds applied in the treatment of, for example oedemas and hypertension, besides the well-known auxiliary agents. Such other compounds may be, for instance, Veratrum- or Rauwolfia alkaloids, e.g. reserpine, rescinnamine or protoveratrine or synthetic hypotensive compounds, e.g. hydralazine, or other diuretics and saluretics, such as the well-known benzothiadiazines, e.g. hydroflumethiazide, bendroflumethiazide, and the like. Potassium-sparing diuretics, e.g. triamterine, may also be used in the preparation of the compositions. For some purposes it may be desirable to add small amounts of aldosterone antagonists, e.g. spironolactone.

Still another object of the invention is to provide a method of preparing the compounds of the invention.

In one embodiment the compounds of the invention are prepared according to the following reaction scheme

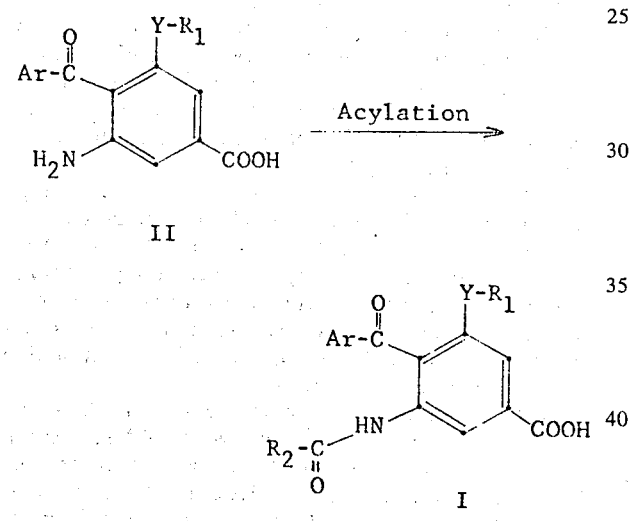

in which formulae the substituents $R_1$, $R_2$, Ar, and Y are as defined before. The reaction is performed by treating the compound of formula II with a compound $R_2COOH$ or a reactive derivative of the latter compound, such as an acid halide, preferably in acid chloride, as ester or an anhydride, if necessary in the presence of acid-binding agents. The isolation of the compounds of formula I can be performed by means of well-known standard procedures.

When esters of the compounds of the formula II are used in the reaction, the compounds of the formula I are obtained as esters. The corresponding free acids may, optionally, be obtained by a subsequent saponification. In the case of the desired product being an ester and the starting material of formula II being the free acid, an esterification can be performed either before or after the acylation process.

The starting compounds of formula II are known or can be prepared by conventional methods for preparing analogous known compounds.

The invention will now be illustrated by the following non-limiting Examples from which the details of the embodiments will be apparent.

EXAMPLE 1

4-Benzoyl-3-n-butoxy-5-formamidobenzoic acid

A solution of 5-amino-4-benzoyl-3-n-butoxybenzoic acid (1.0 g) and formic acid (10 ml) is stirred at room temperature for 24 hours. After cooling, the resulting precipitate is collected and washed with ice-cold formic acid followed by cold water. After drying and recrystallization from ethanol, 4-benzoyl-3-n-butoxy-5-formamidobenzoic acid is obtained with a melting point of 180°–183° C.

EXAMPLES 2–12

By following the procedure described in Example 1, but replacing the 5-amino-4-benzoyl-3-n-butoxybenzoic acid with other 3-substituted 5-amino-4-benzoylbenzoic acids, the 3-substituent of which are as defined in Table I below, the corresponding 3-substituted 4-benzoyl-5-formamidobenzoic acids of Table I are obtained.

Table I

| Ex. No. | 3-substituent | M.p.° C of 3-substituted 4-benzoyl-5-formamidobenzoic acids |
|---|---|---|
| 2 | n-propoxy | 144–145 |
| 3 | benzyloxy | 212–212.5 |
| 4 | ethoxy | 163–165 |
| 5 | 2-pyridylmethoxy | 198–199 |
| 6 | 3-thienylmethoxy | 206–208 |
| 7 | benzylthio | 178–180 |
| 8 | n-propylthio | 168.5–170 |
| 9 | n-butylthio | 155–156 |
| 10 | isopentylthio | 150–151 |
| 11 | allylthio | 182.5–183.5 |
| 12 | 2-phenethyl | 153–154 |

EXAMPLE 13

5-Acetamido-4-benzoyl-3-n-butoxybenzoic acid

A mixture of 5-amino-4-benzoyl-3-n-butoxybenzoic acid (0.8 g), acetic anhydride (0.8 ml) and acetic acid (8.0 ml) is heated on a steam-bath for 1 hour. After cooling, the resulting solution is poured into water (about 20 ml) and the mixture is left at room temperature for about 20 hours. The resulting precipitate is collected by filtration and washed with water. After drying and recrystallization twice from aqueous ethanol, 5-acetamido-4-benzoyl-3-n-butoxybenzoic acid is obtained with a melting point of 177°–178° C.

EXAMPLES 14–17

By following the procedure described in Example 13, but replacing the 5-amino-4-benzoyl-3-n-butoxybenzoic acid with 5-amino-4-benzoyl-3-benzyloxybenzoic acid, 5-amino-4-benzoyl-3-benzylthiobenzoic acid, 3-allylthio-5-amino-4-benzoylbenzoic acid and 5-amino-4-benzoyl-3-(2-phenethyl)- benzoic acid respectively, 5-acetamido-4-benzoyl-3-benzyloxybenzoic acid, 5-acetamido-4-benzoyl-3-benzylthiobenzoic acid, 5-acetamido-3-allylthio-4-benzoylbenzoic acid and 5-acetamido-4-benzoyl-3-(2-phenethyl) benzoic acid are obtained with melting points of 222.5°–223.5° C, 197.5°–198.5° C, 210°–211° C and 183°–184° C respectively.

EXAMPLE 18

4-Benzoyl-3-benzyloxy-5-propionylamidobenzoic acid

A solution of 5-amino-4-benzoyl-3-benzyloxybenzoic acid (0.7 g), propionyl chloride (0.3 ml) and pyridine (0.5 ml) in chloroform (10 ml) is refluxed for about 2 hours and is then evaporated in vacuo. The residue is triturated with 1 N hydrochloric acid (10 ml) and the resulting precipitate is collected by filtration and washed with water. After drying and recrystallization twice from ethanol, 4-benzoyl-3-benzyloxy-5-propionylamidobenzoic acid crystallizing with 1 mole of ethanol is obtained with a melting point of 172°–173.5° C.

EXAMPLE 19

By replacing in Example 18 5-amino-4-benzoyl-3-benzyloxybenzoic acid with an equimolar amount of 5-amino-4-benzoyl-3-(2-phenethyl) benzoic acid and following the procedure described, 4-benzoyl-3-(2-phenethyl)-5-propionylamidobenzoic acid is obtained with a melting point of 168°–168.5° C.

EXAMPLE 20

4-Benzoyl-3-benzyloxy-5-chloroacetamidobenzoic acid

By replacing in Example 18 propionyl chloride with an equimolar amount of chloroacetyl chloride and following the procedure described, 4-benzoyl-3-benzyloxy-5-chloroacetamidobenzoic acid is obtained with a melting point of 214°–215.5° C.

EXAMPLE 21

4-Benzoyl-3-benzyloxy-5-trifluoroacetamidobenzoic acid

By replacing in Example 18 propionyl chloride with an equimolar amount of trifluoroacetic anhydride and performing the reaction for 24 hours at room temperature, 4-benzoyl-3-benzyloxy-5-trifluoroacetamidobenzoic acid is obtained with a melting point of 213° C.

EXAMPLE 22

4-Benzoyl-3-benzyloxy-5-dimethylaminoacetamidobenzoic acid

A mixture of 4-benzoyl-3-benzyloxy-5-chloroacetamidobenzoic acid (0.85 g) and 20% w/w aqueous dimethylamine (10 ml) is left at room temperature for 20 hours and is then evaporated in vacuo. The residue is triturated with conc. hydrochloric acid (about 5 ml) and the resulting precipitate is collected by filtration and dried. After recrystallization from methyl cellosolve, 4-benzoyl-3-benzyloxy-5-dimethylaminoacetamidobenzoic acid hydrochloride is obtained with a melting point of 264.5°–265.5° C.

What we claim is:

1. A compound having the general formula:

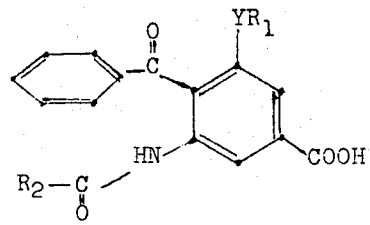

I in which $R_1$ represents a straight or branched $C_1$–$C_6$ alkyl or alkenyl radical, or a $C_1$–$C_3$ alkyl radical substituted with phenyl; $R_2$ stands for hydrogen or a $C_1$–$C_3$ alkyl radical, optionally being substituted with halogen or a di-(lower alkyl) amino radical; Y stands for oxygen; and the pharmaceutically acceptable, non-toxic salts thereof.

2. A compound of claim 1, in which $R_1$ represents benzyl and $R_2$ stands for a dimethylamino radical.

3. A compound having the general formula:

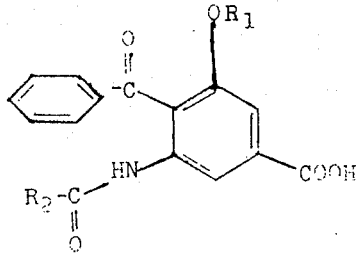

in which $R_1$ represents a straight or branched $C_1$–$C_6$ alkyl or alkenyl radical, or a $C_1$–$C_3$ alkyl radical substituted with phenyl and $R_2$ stands for hydrogen or a $C_1$–$C_3$ alkyl radical, optionally being substituted with halogen; and the pharmaceutically acceptable, non-toxic salts thereof.

4. 4-Benzoyl-3-n-butoxy-5-formamidobenzoic acid and pharmaceutically acceptable, non-toxic salts thereof.

5. 4-Benzoyl-3-benzyloxy-5-formamidobenzoic acid and pharmaceutically acceptable, non-toxic salts thereof.

6. 5-Acetamido-4-benzoyl-3-n-butoxybenzoic acid and pharmaceutically acceptable, non-toxic salts thereof.

7. 5-Acetamido-4-benzoyl-3-benzyloxybenzoic acid and pharmaceutically acceptable, non-toxic salts thereof.

* * * * *